(12) United States Patent
Berg et al.

(10) Patent No.: US 9,233,191 B2
(45) Date of Patent: Jan. 12, 2016

(54) DRUG-COATED MEDICAL DEVICES

(71) Applicant: Innora GmbH, Berlin (DE)

(72) Inventors: Madeleine Caroline Berg, Berlin (DE); Thomas Speck, Berlin (DE)

(73) Assignee: InnoRa GmbH, Berlin (DE)

( * ) Notice: Subject to any disclaimer, the term of this patent is extended or adjusted under 35 U.S.C. 154(b) by 0 days.

(21) Appl. No.: 14/359,754

(22) PCT Filed: Dec. 14, 2012

(86) PCT No.: PCT/EP2012/075563
§ 371 (c)(1),
(2) Date: May 21, 2014

(87) PCT Pub. No.: WO2013/092416
PCT Pub. Date: Jun. 27, 2013

(65) Prior Publication Data
US 2014/0322291 A1    Oct. 30, 2014

(30) Foreign Application Priority Data
Dec. 23, 2011    (EP) .................... PCT/EP2011/073946

(51) Int. Cl.
*A61L 29/08* (2006.01)
*A61L 29/14* (2006.01)
*A61L 29/16* (2006.01)
*A61M 25/10* (2013.01)

(52) U.S. Cl.
CPC ............... *A61L 29/08* (2013.01); *A61L 29/14* (2013.01); *A61L 29/16* (2013.01); *A61M 25/104* (2013.01); *A61L 2300/416* (2013.01); *A61L 2300/452* (2013.01); *A61L 2400/10* (2013.01); *A61M 2025/105* (2013.01)

(58) Field of Classification Search
CPC ............... A61L 2300/416; A61L 2300/452; A61L 2400/10; A61L 29/08; A61L 29/14; A61L 29/16; A61M 2025/105; A61M 25/104
See application file for complete search history.

(56) References Cited

U.S. PATENT DOCUMENTS

| | | | |
|---|---|---|---|
| 5,199,951 A | 4/1993 | Spears | |
| 5,304,121 A | 4/1994 | Sahatjian | |
| 5,370,614 A | 12/1994 | Amundson et al. | |
| 5,893,840 A | 4/1999 | Hull et al. | |
| 6,306,166 B1 | 10/2001 | Barry et al. | |
| 6,419,692 B1 | 7/2002 | Yang et al. | |
| 6,524,347 B1 | 2/2003 | Myers et al. | |
| 6,616,650 B1 | 9/2003 | Rowe | |
| 7,108,684 B2 | 9/2006 | Farnan | |
| 7,445,792 B2 | 11/2008 | Toner et al. | |
| 7,750,041 B2 | 7/2010 | Speck et al. | |
| 8,092,822 B2* | 1/2012 | Pacetti et al. | 424/423 |
| 2003/0203991 A1* | 10/2003 | Schottman et al. | 523/334 |
| 2004/0213826 A1 | 10/2004 | Marx et al. | |
| 2005/0004663 A1* | 1/2005 | Llanos | A61L 31/16 623/1.46 |
| 2005/0113687 A1 | 5/2005 | Herweck et al. | |
| 2008/0118544 A1 | 5/2008 | Wang | |
| 2008/0255509 A1* | 10/2008 | Wang | 604/103.02 |
| 2009/0246252 A1 | 10/2009 | Arps et al. | |
| 2010/0086579 A1* | 4/2010 | Yan et al. | 424/423 |
| 2010/0179475 A1 | 7/2010 | Hoffmann et al. | |
| 2010/0209473 A1 | 8/2010 | Dhont et al. | |
| 2011/0274732 A1 | 11/2011 | Srivastav et al. | |

FOREIGN PATENT DOCUMENTS

| | | | |
|---|---|---|---|
| EP | 1913962 A1 | 4/2008 | |
| EP | 2386322 A2 | 11/2011 | |
| WO | WO-94/23787 A1 | 10/1994 | |
| WO | WO-95/03083 A1 | 2/1995 | |
| WO | WO-2004/028582 A1 | 4/2004 | |
| WO | WO-2009/018816 A2 | 2/2009 | |
| WO | WO-2009/066330 A1 | 5/2009 | |
| WO | WO-2010/040064 A1 | 4/2010 | |
| WO | WO 2012/017449 A1 * | 2/2012 | A61K 31/436 |

OTHER PUBLICATIONS

International Search Report and Written Opinion in Application No. PCT/EP2012/075563 dated Feb. 1, 2013.
International Preliminary Report on Patentability in Application No. PCT/EP2012/075563 dated Nov. 28, 2013.
Cremers et al., "Comparison of Two Different Paclitaxel-Coated Balloon Catheters in the Porcine Coronary Restenosis Model", Clin Res Cardiol, 98:325-330, 2009.
Scheller et al., "Paclitaxel Balloon Coating—A Novel Method for Prevention and Therapy of Restenosis", Circulation 2004, 110: 810-814.

* cited by examiner

*Primary Examiner* — Aradhana Sasan
(74) *Attorney, Agent, or Firm* — Marshall, Gerstein & Borun LLP

(57) ABSTRACT

The present invention is related to a medical device carrying at least on a portion of its surface at least one drug or drug preparation and at least one lipophilic lubricant at a ratio of 0.1-500% by weight of the at least one lubricant in relation to 100% by weight of the drug, wherein the at least one drug is selected of paclitaxel, arsenic trioxide, and lipophilic derivatives of corticoids and selected Limus drugs, and the at least one lipophilic lubricant is a $C_6$-$C_{30}$-monocarboxylic acid salt.

23 Claims, No Drawings

US 9,233,191 B2

DRUG-COATED MEDICAL DEVICES

FIELD OF THE INVENTION

The invention relates to the transfer of a drug loosely adhering to the surface of a medical device to a site inside the body, usually the wall of a diseased blood vessel. The most frequent application is local drug therapy during percutaneous transluminal angioplasty (PTA) or percutaneous transluminal coronary angioplasty (PTCA). These interventions are performed to restore blood flow in stenotic or occluded blood vessels, usually in arteries. A catheter is introduced into a major artery. At the distal end the catheter carries a cylindrical balloon in a folded state with very small diameter. In this state the balloon can enter or pass the stenotic or occluded segment of the blood vessel. Once positioned in the narrowed segment, the balloon is inflated with low or high pressure to expand the lumen of the blood vessel to its original diameter. Simultaneously, a drug may be transferred to the vessel wall to prevent early and late re-narrowing due to the deposition of thrombi and/or hyperproliferation of the injured vessel wall.

BACKGROUND

Medical devices may contain drugs either to improve the tolerance, efficacy, or in vivo life-time of the device or use the device as a carrier for the drug. In either case the dose density (e.g. mg drug/mg device or mg drug/$mm^2$ device surface), chemical stability, adherence, premature loss of drug, release rate, and total amount released are important and often critical features of the drug formulation. These properties are the more critical the more the requirements during production and application of the device vary or may even be contradictory. Drug-coated angioplasty catheters are typical examples: the drug coating must adhere firmly to tolerate mechanical stress during production including folding of balloons, crimping of stents, packaging, shipping to customers, and during final application, which involves passage through a narrow hemostatic valve, an introductory sheath or guiding catheter, and a variable distance of possibly tortuous and narrow blood vessels. When the balloon is inflated the drug should be released as rapidly and as completely as possible within a minute or less. The problem was demonstrated by Cremers et al. (Cremers B, Biedermann M, Mahnkopf D, Böhm M, Scheller B. Comparison of two different paclitaxel-coated balloon catheters in the porcine coronary restenosis model. Clin Res Cardiol 2009; 98:325-330), who retrieved as much as 50% of the dose from balloons after expansion for one minute in coronary arteries of pigs, whereas other catheters coated with the same drug and dose but in a different formulation released more than 95%. Almost perfect results (i.e., loss of only 10% of dose and only about 10% residual drug on the balloon after expansion in an artery) were achieved with a rigid prototype balloon (Scheller B, Speck U, Abramjuk C, Bernhardt U, Böhm M, Nickenig G. Paclitaxel balloon coating—a novel method for prevention and therapy of restenosis. Circulation 2004; 110: 810-814). The application of the same coating composition to more flexible modern balloon catheters resulted in problems, i.e., larger premature loss of the drug.

Another problem relates to the increased roughness of drug-coated medical devices, e.g., balloon catheters and stents. Usually, the surface is very smooth, which is accomplished by careful polishing in case of stents. In case of catheters a thin slippery hydrophilic layer may be coated on the surface to reduce friction inside guiding catheters and tortuous and narrowed vessel segments.

PRIOR ART

Protection from Premature Loss of Drug

Premature loss of a drug from a balloon is a major problem, which has been addressed by a variety of methods. Some of them are mechanical, e.g. use of protection tubes, sleeves, or envelops. Examples are U.S. Pat. No. 5,370,614, U.S. Pat. No. 6,306,166, and U.S. Pat. No. 6,616,650 disclosing various protective sheaths which are retracted before the balloon is inflated or U.S. Pat. No. 6,419,692 proposing a cover which bursts during balloon expansion. A different approach is taken in U.S. Pat. No. 5,893,840 disclosing structured balloon membranes with tiny cavities, WO 94/23787 with roughened balloon membranes to enhance the adherence of coating, or more recently U.S. Pat. No. 7,108,684 proposing a pouch which protects the drug-containing layer on the balloon and WO 2009/066330 disclosing methods placing the drug selectively under the folds of a folded balloon. Although efficacious, these methods have the disadvantages of increasing the complexity and cost of production or making handling of the devices more difficult or adding to the diameter of the devices (which must be kept as small as possible to facilitate passage through stenotic lesions). In some embodiments the protective membranes or perforated membranes prevent homogeneous transfer of the drug to the tissue or even put the patient at risks.

Other approaches use either physical or chemical methods to control the release of drugs from a balloon surface, e.g., U.S. Pat. No. 5,304,121 describes a hydro-gel which releases the drug only after exposure to a triggering agent; U.S. Pat. No. 5,199,951 relies on thermal activation; according to U.S. Pat. No. 7,445,792 a lipophilic 'hydration inhibitor' protects water-soluble drugs from premature release; and according to U.S. Pat. No. 5,370,614 a viscous matrix protects the drug from premature release, however, the viscous matrix must be protected by a sheath during passage to the stenotic vessel segment. None of the methods has been tested in practice and proven to fulfill the requirements for fast, reliable, and complete drug transfer to the target tissue.

Hydrogels do reduce friction, but on the other hand they must be protected.

Therefore, a need remains for a method or formulation which protects the coat-in from premature losses during production, handling, and on the way to the lesion and still allows immediate and complete release of the active ingredient at a location and point in time determined by the user.

Furthermore, a need exists to improve the lubricity of the coated device in the area of coating, a problem which has hardly been recognized and not been addressed in a satisfactory way. Hydrogels have been proposed as coating of medical devices (WO 95/03083, U.S. Pat. No. 5,199,951, US 2009/0246252, U.S. Pat. No. 6,524,347). Hydrogels may not only provide a matrix for a drug but also serve as a lubricant in a wet state. Disadvantages are the need to be provided with a sufficient water content (to display lubricity) or to swell in an aqueous medium to turn lubricant. Another important disadvantage is the reduced adherence to the surface of the medical device if the hydrogel is in its functional (i.e., humid) state. If provided in a humid state chemical stability of drugs and sterility are difficult to maintain.

An advantageous way of controlling both the frictional force of a coating's surface and the adherence and release of a drug from a medical device, e.g., an angioplasty balloon, is the selection of a suitable formulation and coating which do not require mechanical protection, or additional physical or chemical interaction with the coating except the usual operation of the device, e.g., inflation of a folded balloon to induce the release of the drug. The conflicting objectives of sufficient dose, low profile of folded balloons, low friction, perfect adherence before use and immediate release at the site of action make the selection of suitable compositions and coating methods a difficult task. An ex-ample of prior art is US 2008/0118544 reciting an excessive number of substances and substance classes. EP 2386322 claims oils, fats, and waxes, preferably unsaturated fatty acids, as additives to coating formulations for balloon catheters. U.S. Pat. No. 7,445,792 discloses the use of 'hydration inhibitors' not applicable to the preferred class of very lipophilic drugs which require 'hydration enhancers' or 'dispersion and dissolution enhancers' as e.g. disclosed in WO 2004/028582. Although the hydrophilic additives (which may be regarded as 'hydration enhancers') work quite well on certain balloon membranes (Scheller B, Speck U, Abramjuk C, Bernhardt U, Böhm M, Nickenig G. Paclitaxel balloon coating—a novel method for prevention and therapy of restenosis. Circulation 2004; 110: 810-814) the adherence of the drug admixed to these excipients on various modern PTA or PTCA balloons is either too weak or too tight, resulting in premature loss of a major proportion of the drug or incomplete release at the target site. Prior art coatings are usually distinctly rougher than the surface of the uncoated device, none of the compositions has been tested in respect of lubricity, and no guidance is disclosed on how to obtain a smooth surface which ensuring low friction in a dry and wet state.

PRIOR ART

Lubricants

Lubricants generally ensure that tablet formation and ejection can occur with low friction between the solid and die wall. Common minerals like talcum or silica, and fats, e.g., vegetable stearin, magnesium stearate or stearic acid are the most frequently used lubricants in pharmaceuticals. Lubricants are agents added in small quantities to tablet and capsule formulations to improve certain processing characteristics. There are three roles identified with lubricants as follows:

1. True lubricant role: To decrease friction at the interface between a tablet's surface and the die wall during ejection and reduce wear on punches & dies.

2. Anti-adherent role: To prevent sticking to punch faces or in the case of encapsulation and to prevent sticking to machine dosators, tamping pins, etc.

3. Glidant role: To enhances product flow by reducing interparticulate friction.

There are two major types of lubricants:

1. Hydrophilic—generally poor lubricants, which have no glidant or anti-adherent properties.

2. Lipophilic—the most widely used lubricants today are of the lipophilic category. Lipophilic lubricants are generally good lubricants and are usually effective at relatively low concentrations. Many also have both anti-adherent and glidant properties. For these reasons, lipophilic lubricants are used much more frequently than hydrophilic compounds. The most common lubricant is magnesium stearate.

Lubricants are admixed as solids to powders or granulates or other solid pharmaceutical formulations for oral or enteral administration or to ointments.

No documents can be found that hint to the advantages of lubricants as additives to formulations for local drug therapy during percutaneous transluminal angioplasty (PTA) or percutaneous transluminal coronary angioplasty (PTCA) or provide any guidance on how to add the poorly soluble lubricants to pharmaceutical formulations suitable for the coating of medical devices. Tolerance following intravascular administration has not been considered and no difference is made between lubricants which may be administered parenterally and those for which intravasclular use must be excluded, for example because they are not excreted. According to US 2005/0113687 [0036, tab. 1+2] certain fats and oils improve the adherence and release of drugs on the surface of medical devices and enhance the transfer of drugs into the tissue. Lipids, oils and fatty acids are also proposed in US 20080255509 [0102-0104] and lipids and oils were already proposed in U.S. Pat. No. 7,750,041. Lipids are a major component of drug coating of stents as disclosed in US 2011/0274732 [0089] combined with aromatic additives. Lubricious property of fat coatings is mentioned [0041]. Although balloons for angioplasty are considered the release rate of the drug from the coating is too slow to be useful on a balloon which is usually inflated for only one minute. Furthermore, US20100209473 describes drug-coated balloon catheters with a matrix of chemically hardened oil or fat.

EP 1 913 962 A1 discloses a variety of pharmaceutical compositions containing gemcitabine compounds as active ingredients which among other applications are also used to coat expandable medical devices for intravascular use. Optionally, the gemcitabine compound is mixed with other drugs or commonly known excipients including lubricants, the latter listed without differentiation of compounds suitable or unsuitable for vascular use, and without pointing out how a suitable coating may be achieved or which dose or quantitative composition to use for the formulation. Similarly, in US 2004/0213826 a broad range of different commonly known pharmaceutical excipients including lubricants is named [0051] as potential carriers for HDAC inhibitors on various medical devices including angioplasty balloon catheters. The same applies to WO2010/040064 [0087] for compositions with myolimus as active ingredient.

Although lubricants are mentioned in US 2010/179475 the composition of the coating is distinctly different and does not satisfy the above mentioned purpose since the lubricant is placed between the balloon surface and the coating containing the drug [0270].

PRESENT INVENTION

The problem underlying the present invention was to provide a drug coated medical device with a reduced frictional force of the coating's surface and an improved adherence of the drug without negative effect on the release of the drug at the target site.

Accordingly, the invention provides a medical device carrying at least on a portion of its surface at least one drug and at least one lipophilic lubricant at a ratio of 0.1-500% by weight of the at least one lipophilic lubricant in relation to 100% by weight of the drug, wherein the at least one drug is selected from paclitaxel, arsenic trioxide, lipophilic derivatives of corticoids and sirolimus, everolimus, zotarolimus, biolimus, temsirolimus and the at least one lipophilic lubricant is a $C_6$-$C_{30}$-monocarboxylic acid salt and the at least one drug and the at least one lubricant are applied at the same time in the same solvent or mixture of solvents or the drug-coated device is coated with an additional layer of the at least one lubricant.

In other words, the problem was solved by a medical device carrying at least on a portion of its surface at least one drug and at least one lipophilic lubricant at a ratio of 0.1-500% by weight of the at least one lipophilic lubricant in relation to 100% by weight of the drug. Preferred common lubricants are lipophilic with a partition coefficient between n-butanol and water >10 or are almost insoluble in both most organic and aqueous solvents (<10 mg/ml, 20° C.). The at least one drug is a natural, semi-synthetic or synthetic drug, preferably semi-synthetic or synthetic drug, and selected from taxanes, thalidomide, arsenic trioxide, statins, corticoids and lipophilic derivatives of corticoids and Limus drugs. Below, the terms "drug" and "active drug" are used interchangeable if the invention is concerned. In one preferred embodiment the lubricant is less lipophilic as the drug.

The at least one lipophilic lubricant is a monocarboxylic acid salt (chain length $C_6$-$C_{30}$), preferably with $Mg^{2+}$, $Ca^{2+}$, $Zn^{2+}$ or ammonium ($NH^{4+}$), more preferably with $Mg^{2+}$, $Ca^{2+}$ or $Zn^{2+}$. The $C_6$-$C_{30}$-monocarboxylic acid may be saturated or may have one or more double bonds (unsaturated). Preferred $C_6$-$C_{30}$-monocarboxylic acid salts are magnesium stearate, calcium stearate, zinc stea-rate, magnesium palmitate, calcium palmitate, zinc palmitate, magnesium myristate, calcium myristate, magnesium laurate, calcium laurate, magnesium caprinate, calcium caprinate, magnesium caprylate, calcium caprylate, magne-sium oleate, calcium oleate, magnesium palmitoleate or calcium palmitoleate. Optionally, the salts are admixed to at least one of stearic acid, palmitic acid, lauric acid, capric acid, caprylic acid, oleic acid, palmitoleic acid, stearic alcohol, palmitic alcohol, lauric alcohol, magnesium acetate and/or calcium acetate.

During testing of a large variety of coating methods, additives and drug combinations the surprising discovery was made that certain lipophilic lubricants added to less or even more lipophilic and more or less water-soluble drugs, such as inhibitors of cell proliferation or inhibitors of neovascularization in a defined mass ratio significantly reduce frictional force and increase adherence of the drug to a variety of state-of-the art balloon membranes during handling and on the way to the target lesion even if the target lesion is located far away from the site where the device first enters a blood-filled introductory sheath, guiding catheter, or vessel containing rapidly flowing blood. Furthermore, methods were developed allowing the dissolution and homogeneous distribution of the most efficacious but least soluble lubricants such as magnesium stearate while maintaining the favorable properties of the dry product.

Alternatively, the problems relating to the extremely low solubility of the salts mentioned above in both aqueous and organic solvents were overcome by the selection of fatty acid salts of pharmaceutically acceptable organic bases, pref-erentially monovalent amines. Examples are ethanolamine, aminopropandiole, serinol, glucosamine, tris(tris(hydroxymethyl)aminomethane), methylglu-camine, basic amino acid, combined with the above mentioned $C_6$-$C_{30}$-monocarboxylic acids. These compounds meet the requirements in respect of chemical stability, adherence to the medical device, impact on the adherence and release of drugs, and biocompatibility. Preferred is tris stearate. Another preferred compound is lysine stearate, more preferred is arginine stearate Thus, at least one lipophilic lubricant in an amount of 0.1-500% by weight is used as a frictional force reducer and adherence improver for drugs coated on a medical device during this initial step of introducing the medical device into the vasculature. The wording "at least one lipophilic lubricant" includes single lubricants but also mixtures of different lubricants. Other substances or pharmaceutical compounds may be added to further adjust the properties of the product to the demand in respect of stability or other pharmaceutical requirements and tolerance etc.

Examples of active drugs are inhibitors of cell proliferation such as taxanes, preferably paclitaxel, docetaxel and protaxel, more preferably paclitaxel or ar-senic trioxide. Alternatively, specific inhibitors of neovascularization such as thalidomide, statins like atorvastatin, cerivastatin, fluvastatin or anti-inflammatory drugs like corticoids or even more preferred lipophilic derivatives of corticoids such as betamethasone diproprionate or dexamethasone-21-palmitate, and Limus drugs, especially immuno-suppressants like mTOR inhibitors such as sirolimus, everolimus, zotarolimus, biolimus, temsirolimus, most preferred sirolimus, are used. That is, a preferred group of drugs consists of paclitaxel, arsenic trioxide, lipophilic derivatives of corticoids and the Limus drugs sirolimus, everolimus, zotarolimus, biolimus, temsirolimus having the more preferred sub-groups paclitaxel, arsenic trioxide and Limus drugs siroli-mus, everolimus, zotarolimus, biolimus, temsirolimus, wherein sirolimus is the most preferred one out of these Limus drugs. Various drugs may be applied or combined if different pharmacological actions are required or efficacy or tolerance is to be improved. Drugs can also be drug preparations". Thus, the wording "at least one drug (or drug preparation)" means that single drugs but also mixtures of different drugs are included. Preferred drugs are either lipophilic (partition coefficient between n-butanol and water >10) or display very poor water solubility (<10 mg/ml, 20° C.). Preferred are those drugs which in dry state are chemically stable during long-term storage, e.g., paclitaxel and other taxanes, statins, thalidomide, corticosteroids and lipophilic derivatives of corticoids. Preferred among these are paclitaxel, protaxel and docetaxel with paclitaxel being the most preferred drug. Drugs are natural, semi-synthetic or synthetic. Preferred drugs are semisynthetic or synthetic drugs. Drugs must be used in a dose range providing the desired effect without compromising the technical features of the coated balloon such as flexibility. A preferred dose range is between 1 and 10 µg/mm² balloon surface, most preferred up to 6 µg/mm².

Lipophilic lubricants are usually solid at temperatures up to 40° C. Preferred—as mentioned above—are salts of mocarboxylic acids like magnesium stearate, calcium stearate, zinc stearate, magnesium palmitate, calcium palmitate, zinc palmitate, magnesium myristate, calcium myristate, magnesium laurate, calcium laurate, magnesium caprinate, calcium caprinate, magnesium caprylate, calcium caprylate, magnesium oleate, calcium oleate, magnesium palmitoleate and calcium palmitoleate, most preferred magnesium stearate, calcium stearate, magnesium palmitate, or calcium palmitate. Magnesiumcaprylate is particularly preferred if higher solubility is required. The wording "at least one lipophilic lubricant" includes single lubricants but also mixtures of different lubricants. Optional mixtures with stearic acid, palmitic acid, lauric acid, capric acid, caprylic acid, oleic acid, palmitoleic acid, stearic alcohol, palmitic alcohol, lauric alcohol, magnesium acetate and/or calcium acetate are also included.

Combinations of these lubricants with the above-mentioned drugs showed reduced frictional force and improved adherence, they are well tolerated and efficacious at the site where they are deposited, e.g. in the arterial wall and the adjacent tissue.

The dose of the lubricant on the surface of a medical device may be defined in respect of the therapeutic drug. Preferred relationships (weight/weight) are 0.1-500% lubricant of the weight of the drug. For example, if the dose density of the drug is 2 µg/mm² device surface the amount of lubricant is 0.002-10.0 µg/mm². Higher proportions of the lubricant may be selected if either the drug is applied at a dose below 2 µg/mm² device surface or the adherence of the drug to the device surface is further improved. The lubricant load of the device may reach 10 µg/mm². A higher load is possible. Other preferred ranges for the relationship of lubricant to drug on a weight/weight basis are 1-200%, more preferred 1-100%, even more preferred 2-75% and most preferred 2-50% in relation to 100% of the drug. Especially the range of 2-50% on a weight/weight basis reduces friction between coating and e.g. hemostatic valves, introductory sheaths, or guiding catheters and tortuous blood vessels and enhances adherence of drugs to the surface of the device significantly. Usually, lower amounts improve lubricity and adherence correspondingly less, i.e., the more lubricant the lower the frictional force and the better the adherence showing a correlation in the preferred range. The relationship may also be defined in respect of moles: in a preferred embodiment the lubricant is present from 0.2 mole % to 1000 mole % relative to the drug. Higher amounts of the lubricant may be useful.

If more than one drug is used, the total weight of the drugs or the total moles of the drugs serve as the basis for the calculation of the amount of lubricant. If more than one lubricant is used, the total weight of the lubricants or the total moles of the lubricants serve as the basis for the calculation of the amount of the drugs.

Other well tolerated and approved additives and/or excipients may be applied to further improve the mechanical or pharmaceutical properties of the coating. It is a special advantage of the present compositions that they do not require the use of polymers to prevent premature loss of the drug. Nevertheless, small amounts of pharmaceutically acceptable polymers such as polyacrylic acids may be added, e.g., to improve the distribution of the drug on the balloon or adherence of the dry coating during handling. Small amounts mean about 1-20% (w/w) of the drug(s). If polymers are used, substances with low to moderate molecular weight, i.e., 2000 to 50,000 D are preferred.

Usually, drugs and mixtures of drugs with additives are coated on medical devices as liquid formulations in volatile solvents. The choice of solvent is important for the structure of the coating in dry state and adherence and release of the drug from the surface. Preferred volatile organic solvents are acetone, tetrahydrofuran, acetic acid, and various alcohols such as methanol, ethanol, and isopropyl alcohol (isopropanol). Usually, 1 to 30% (volume/volume) water is added. The drug or drugs and the lubricant may be applied at the same time, dissolved in the same solvent or mixture of solvents. That is, the drug(s) and the lubricant are—finally—present within one and the same coating layer, i.e. within one single coating layer. Alternatively, they may be separately dissolved in the same or different solvents and sequentially applied. Preferably, a lubricious surface is achieved in this alternative in that the lubricant is coated on the surface of the drug-coated medical device that is the medical device is coated first with the drug and then with the lubricant., i.e. the drug is—finally—present in one first coating layer and the lubricant is—finally—present in one second coating layer (above the first coating layer).

Overall, the medical device according to the present invention carries at least on a portion of its surface at least one drug and at least one lipophilic lubricant at a ratio of 0.1-500% by weight of the at least one lipophilic lubricant in relation to 100% by weight of the drug, wherein the at least one drug is selected from paclitaxel, arsenic trioxide, lipophilic derivatives of corticoids and sirolimus, everolimus, zotarolimus, biolimus, temsirolimus and the at least one lipophilic lubricant is a $C_6$-$C_{30}$-monocarboxylic acid salt and the at least one drug and the at least one lubricant are applied at the same time in the same solvent or mixture of solvents or the drug-coated device is coated with an additional layer of the at least one lubricant.

In a preferred embodiment, the medical device has been coated with at least one drug and at least one lipophilic lubricant either both together or each separately dissolved in tetrahydrofuran or a mixture of solvents containing more than 25% (v/v) tetrahydrofuran. Optionally, the at least one lipophilic lubricant is dissolved in a different solvent or solvent mixture selected from the above mentioned group of preferred organic solvents and water, i.e. from acetone, acetic acid, water and alcohols. Another preferred embodiment is based on a medical device, which has been coated with at least one drug and at least one lipophilic lubricant either both together or each separately dissolved in acetone or a mixture of solvents containing more than 25% (v/v) acetone. Optionally, the at least one lipophilic lubricant is dissolved in a different solvent or solvent mixture selected from the above mentioned group of preferred organic solvents and water, i.e. from tetrahydrofuran, acetic acid, water and alcohols.

Yet another preferred embodiment is a medical device which has been coated with at least one drug and at least one lipophilic lubricant either both together or each separately dissolved in isopropanol or a mixture of solvents containing more than 25% (v/v) isopropanol. Optionally, the at least one lipophilic lubricant is dissolved in a different solvent or solvent mixture selected from the above mentioned group of preferred organic solvents and water, i.e. from acetone, tetrahydrofuran, acetic acid, water and other alcohols.

Coating solutions with lubricants may contain 0.01-25% (v/v) of volatile acids, e.g., acetic or formic acid. The addition of these volatile acids has been found to be particularly useful if magnesium, calcium, or zinc stearate or magnesium, calcium or zinc palmitate are to be dissolved in the above-mentioned solvents applied for device coating. Other acids and higher concentrations are also possible. Coating with dry particles such as micro- or nanoparticles, crystals, capsules or particles suspended in a liquid preparation is possible but has distinct disadvantages regarding the homogeneity of the drug-containing layer. Coating with particles may be facilitated by a roughened or sticky surface of the medical device.

A variety of coating procedures providing more or less uniform layers on medical devices are known from the literature and are disclosed in patent applications. These include simple dipping, spraying, and methods providing precise doses and homogeneous distributions (e.g., WO 2009/018816) on folded or expanded balloons. Coating may be applied stepwise, either as multiple layers of the same composition or as layers with different compositions, e.g., the drug first and the lubricant second or in the opposite order or lubricant first, drug second and then lubricant again. All these methods may be applied to the formulations of the current invention. Sequential coating with, e.g., the drug first and second the lubricant dissolved in a solvent in which the drug is poorly soluble by, e.g., spraying results in substantially separate layers. Thus, a preferred embodiment is a medical device, which has been sequentially coated with at least one drug and at least one lipophilic lubricant in a way that the drug and the lubricant are not homogeneously mixed.

Furthermore, coated medical devices may be dried under different conditions such as temperature, air flow, gas composition, and pressure at different stages of the production process. They may be stored in water-vapor-tight seals with a separately packed water-absorbing agent within the seal.

Preferred medical devices are balloon catheters, e.g., catheters for angioplasty or coronary angioplasty. Most preferred medical devices are balloon catheters for short use, preferably during an imaging-guided intervention. Short use means that the device is not implanted but removed from the body at the end of the procedure, usually within less than 10 minutes, but never later than a few, preferably 5, hours after the end of the procedure. Catheters may contain balloon membranes made from various polymers and copolymers, e.g., polyamides (nylon 12, pebax), polyesters, polyethylenes, polyurethanes, various polyvinyls, silicones, polyisoprenes, ChronoPrene™ and the like. Independently of the type of material, adherence and release properties of drugs are improved by the addition of lipophilic lubricants.

The medical device carries at least one drug or drug preparation and at least one lipophilic lubricant on at least a portion of its surface which is aimed at coming into close contact with the tissue to be treated, e.g., a balloon at the distal end of a catheter shaft. This means that at least 5%, preferably more than 50%, most preferably more than 90% of the surface is coated. Preferably, the coating is present at least on the surface of the device where it has the widest diameter. If less than 100% of the device's surface is coated, preferably the parts starting with the lowest device diameter are omitted. However, parts such as holds/handles or shafts are omitted per se. A balloon as part of a balloon catheter, which is a preferred medical device, has a central cylindrical part and two opposite conical ends. If less than 100% of the balloon catheter's surface is coated, it is preferred that the cylindrical part is coated and that at least parts of or the complete conical ends remain uncoated.

Another embodiment is a medical device carrying at least on a portion of its surface at least one drug or drug preparation and at least one lipophilic lubricant plus at least one excipient, preferably at least one antioxidant, which may be nordihydroguaiarectic acid, resveratrol, butylated hydroxy toluene, butylated hydroxy anisol, propyl gallate, ascorbyl palmitate at a ratio of 0.1-500% by weight of the at least one drug in relation to 100% by weight of the drug. If antioxidants are added less stable drugs such as various immunosuppressants like sirolimus, everolimus, zotarolimus, biolimus, and temsirolimus may be used with less concern about effects of the immediate chemical environment on their long-term stability.

Below, the invention is described by means of Examples.

Example 1

Nylon-12 balloons, 7.0-80 mm or 4.0-40 mm for percutaneous transluminal angioplasty, were coated in expanded condition either with paclitaxel alone or with paclitaxel plus magnesium stearate (two concentrations), thereafter folded, or coated first with paclitaxel alone, folded, and then with magnesium stearate. Dose density was 3 µg paclitaxel per $mm^2$ balloon surface. Coated balloons were tested for paclitaxel loss during passage through a hemostatic valve, Flexor Check-Flo Introducer 5.5 F Cook Inc, USA, and in stirred blood (37° C.) for one minute. When admixed at sufficient concentration to the coating solution, the lipophilic lubricant reduces friction and improves adhesion of paclitaxel. The results are shown in Table 1.

TABLE 1

| Coating solution | Labeling | Loss on the way to the lesion % of dose | Fit into a narrow protection tube (2.16 mm ID for 7.0-80 MM balloon) |
|---|---|---|---|
| No additive: THF/acetone/H$_2$O/acetic acid 333:333:308:25 (v/v) | Control | 20.4 ± 3.3 | no |

TABLE 1-continued

| Coating solution | Labeling | Loss on the way to the lesion % of dose | Fit into a narrow protection tube (2.16 mm ID for 7.0-80 MM balloon) |
|---|---|---|---|
| Magnesium stearate 2% = 0.02 mg/mg paclitaxel; THF/acetone/H$_2$O/acetic acid 333:333:308:25 (v/v) | MgS-1 | 18.9 ± 2.2 | yes |
| Magnesium stearate 10% = 0.1 mg/mg paclitaxel; THF/acetone/H$_2$O/acetic acid 333:333:308:25 (v/v) | MgS-5 | 14.9 ± 13.7 | yes |
| 1) Paclitaxel; THF/acetone/H$_2$O 333:333:308:25 (v/v) 2) Magnesium stearate 10% = 0.1 mg/mg paclitaxel; ethanol/H$_2$O/acetic acid 750:225:25 (v/v) | MgS-5a | 6.9 ± 4.9 | yes |

Example 2

Maverick 2 (Boston Scientific Corp) PTCA balloon catheters, 3.5-20 mm balloon size, were coated with paclitaxel (50 mg/ml), zinc stearate (1 mg/ml) in tetrahydrofuran/acetone/water/formic acid (487:244:226:43, v/v), 12 µl were homogeneously distributed on the surface of each folded balloon. The balloon catheters were dried at room temperature for 3 hours, and protection tubes, inner diameter 1.05 mm were mounted on the balloons.

Example 3

Fire Star (Cordis Corp) PTCA balloon catheters, hydrophilic, 3.5-20 mm balloon size, were coated with paclitaxel (30 mg/ml), magnesium oleate (10 mg/ml) in acetone/ethanol/water (2+2+1, v/v): 2 times 15 µl were homogeneously distributed on the surface of each folded balloon. The balloon catheters were dried at room temperature for 3 hours, protection tubes, inner diameter 1.10 mm, were mounted on the balloons.

Example 4

Nylon-12 balloons, PTA balloon catheters, 5.0-20 mm balloon size, were coated with paclitaxel (50 mg/ml), magnesium caprylate (25 mg/ml in tetrahydrofuran/acetone/water (333:333:333, v/v): 20 µl were homogeneously distributed on the surface of each expanded balloon. The balloons were folded and protection tubes mounted on the balloons.

Example 5

Folded balloon catheters produced by Creganna, USA, 3.5-20 mm, coated with paclitaxel, 3.3 µg/mm$^2$ balloon surface, were coated with an additional layer of various lubricants in THF/water (2:1) or ethanol or ethanol/water (4:1 or 1:1) at a dose of 0.33 µg/mm$^2$. After complete drying the balloons were inserted into tight PTFE-tubes of identical diameter. After 24 h the maximum force required to withdraw the tubes was measured. The experiment indicates a significant reduction of friction between coating and tube. The reduced friction will be a distinct advantage when the coated balloons are introduced into a guiding catheter and have to pass highly stenotic vessel segments. The results are shown in Table 2.

TABLE 2

| Lubricant | Solvent (for lubricant) | Maximum force (N) | n |
|---|---|---|---|
| None | n/a | 0.75 ± 0.47 | 8 |
| Magnesium stearate | THF/water (2:1) | 0.28 ± 0.20 | 8 |
| Calcium stearate | THF/water (2:1) | 0.36 ± 0.09 | 4 |
| Zinc stearate | THF/water (2:1) | 0.30 ± 0.18 | 4 |
| Magnesium palmitate | THF/water (2:1) | 0.24 ± 0.11 | 4 |
| Magnesium caprylate | ethanol | 0.12 ± 0.03 | 4 |
| Magnesium oleate | ethanol/water (4:1) | 0.16 ± 0.10 | 4 |
| Magnesium acetate (no lubricant) | ethanol/water (1:1) | 0.60 ± 0.34 | 4 |

Example 6

Folded balloon catheters produced by Creganna, USA, 3.5-20 mm, were coated with a homogeneous solution of paclitaxel and magnesium caprylate in, THF/acetone/water to achieve a dose density of 3.3 μg/mm$^2$ balloon surface and 0.66 μg/mm$^2$, respectively. Coated balloons were tested for paclitaxel loss during passage through a hemostatic valve and a 6F Medtronic Launcher JL3.5 guide catheter. Balloons were kept in stirred blood (37° C.) for one minute. The balloons lost 11.6±0.5% of the total paclitaxel. Identical coated balloons were inflated in coronary arteries of pigs; during the procedure 85.9±4.9% of dose was released during the procedure.

Example 7 a-d

The synthesis of fatty acid salts with various amines was performed by mixing the following solutions: meglumine=N-methyl-D-glucamine; Tris=tris(hydroxymethyl)aminomethane; THF=tetrahydrofuran; eth=ethanol; isopr=isopropanol

| | Stearic acid 4.00 g | | Amine | | | | |
|---|---|---|---|---|---|---|---|
| | Solvent 1 | Solvent 2 | | g | Solvent 1 | Solvent 2 | Yield % |
| a | 20 ml eth | 20 ml THF | Arginine | 2.45 | 40 ml eth | 16 ml water | 94.6 |
| b | 20 ml eth | 20 ml THF | Lysine | 2.31 | 20 ml eth | 10 ml water | 94.1 |
| c | 20 ml isopr | 20 ml THF | Meglumine | 2.74 | 10 ml isopr | — | 97.9 |
| d | 20 ml isopr | 80 ml THF | Tris | 1.70 | 50 ml eth | 10 ml isopr | 94.7 |

| Stearic acid salt | Appearance | Melting ° C. | Decomposition ° C. | Solubility at room temperature |
|---|---|---|---|---|
| a Arginine | white powder | | 150 | eth: 1 mg/ml |
| b Lysine | off-white powder | | 150 | water or eth: 0.3 mg/ml |
| c Meglumine | white powder | 148 | | water: 1 mg/ml eth: 5 mg/ml |
| d Tris | white crystals | 128 | | eth: 10 mg/ml acetone: 0.5 mg/ml |

The invention claimed is:

1. A medical device carrying at least on a portion of its surface at least one drug and at least one lipophilic lubricant at a ratio of 0.1%-500% by weight of the at least one lipophilic lubricant in relation to 100% by weight of the drug, wherein the at least one drug is selected from the group consisting of paclitaxel, arsenic trioxide, lipophilic derivatives of corticoids, sirolimus, everolimus, zotarolimus, biolimus, temsirolimus, the at least one lipophilic lubricant is a $C_6$-$C_{30}$-monocarboxylic acid salt, and the at least one drug and the at least one lubricant are applied at the same time in the same solvent or mixture of solvents or the drug-coated device is coated with an additional layer of the at least one lubricant.

2. The medical device according to claim 1, wherein the $C_6$-$C_{30}$-monocarboxylic acid salt is a magnesium, calcium, zinc, or ammonium salt.

3. The medical device according to claim 1, wherein the $C_6$-$C_{30}$-monocarboxylic acid salt is a salt of a monovalent organic base.

4. The medical device according to claim 1, wherein the $C_6$-$C_{30}$-monocarboxylic acid salt is selected from the group consisting of magnesium stearate, calcium stearate, zinc stearate, magnesium palmitate, calcium palmitate, zinc palmitate, magnesium myristate, calcium myristate, magnesium laurate, calcium laurate, magnesium caprinate, calcium caprinate, magnesium caprylate, calcium caprylate, magnesium oleate, calcium oleate, magnesium palmitoleate, and calcium palmitoleate.

5. The medical device according to claim 1, wherein the $C_6$-$C_{30}$-monocarboxylic acid salt is admixed to one or more components selected from the group consisting of stearic acid, palmitic acid, lauric acid, capric acid, caprylic acid, oleic acid, palmitoleic acid, stearic alcohol, palmitic alcohol, lauric alcohol, magnesium acetate, and calcium acetate.

6. The medical device according to claim 1, wherein the device is an angioplasty balloon catheter for short use.

7. The medical device according to claim 1, wherein the at least one drug is more lipophilic than the at least one lipophilic lubricant.

8. The medical device according to claim 1, wherein the at least one drug is sirolimus.

9. The medical device according to claim 1, wherein the lipophilic derivative of a corticoid is selected from betamethasone dipropionate or dexamethasone-21-palmitate.

10. The medical device according to claim 1, wherein a lipophilic lubricant load is up to 10 μg/mm$^2$ of coated device surface.

11. The medical device according to claim 1, which has been coated with at least one drug and at least one lipophilic lubricant either both together dissolved in tetrahydrofuran or a mixture of solvents containing more than 25% (v/v) tetrahydrofuran or each separately dissolved optionally selecting a different solvent or mixture thereof for the at least one lipophilic lubricant from the group consisting of acetone, acetic acid, water, and alcohols.

12. The medical device according to claim 1, which has been coated with at least one drug and at least one lipophilic lubricant both together dissolved in acetone or a mixture of solvents containing more than 25% (v/v) acetone or each separately dissolved, optionally selecting a different solvent or mixture thereof for the at least one lipophilic lubricant from the group consisting of tetrahydrofuran, acetic acid, water, and alcohols.

13. The medical device according to claim 1, which has been coated with at least one drug and at least one lipophilic lubricant either both together dissolved in isopropanol or a mixture of solvents containing more than 25% (v/v) isopropanol or each separately dissolved optionally selecting a different solvent or mixture thereof for the at least one lipophilic lubricant from the group consisting of acetone, tetrahydrofuran, acetic acid, water, and alcohols other than isoproponal.

14. The medical device according to claim 1, which has been coated with at least one drug and at least one lipophilic lubricant either both together dissolved in a solvent or a mixture of solvents, or each separately dissolved optionally selecting a different solvent for the at least one drug, wherein the solvent or mixture of solvents additionally contains more than 0.01%-25% (v/v) acetic acid or formic acid.

15. The medical device according to claim 1, which has been sequentially coated first with at least one drug and thereafter with at least one lipophilic lubricant in a way that the drug and the lubricant are not homogeneously mixed.

16. The medical device according to claim 1, which has been coated with at least one drug and at least one lubricant plus at least one additional excipient.

17. The medical device according to claim 16, wherein the additional excipient is an antioxidant.

18. The medical device according to claim 1, wherein the at least one lipophilic lubricant is contained at a ratio of 1%-200% by weight in relation to 100% by weight of the at least one drug.

19. The medical device according to claim 1, wherein the at least one lipophilic lubricant is contained at a ratio of 1%-100% by weight in relation to 100% by weight of the at least one drug.

20. The medical device according to claim 1, wherein the at least one lipophilic lubricant is contained at a ratio of 2%-75% by weight in relation to 100% by weight of the at least one drug.

21. The medical device according to claim 1, wherein the at least one lipophilic lubricant is contained at a ratio of 2%-50% by weight in relation to 100% by weight of the at least one drug.

22. The medical device according to claim 1, wherein the at least one drug is semi-synthetic, or synthetic.

23. The medical device according to claim 1, wherein the at least one drug is natural.

* * * * *

UNITED STATES PATENT AND TRADEMARK OFFICE
CERTIFICATE OF CORRECTION

PATENT NO. : 9,233,191 B2
APPLICATION NO. : 14/359754
DATED : January 12, 2016
INVENTOR(S) : Madeleine Caroline Berg et al.

Page 1 of 1

It is certified that error appears in the above-identified patent and that said Letters Patent is hereby corrected as shown below:

In the Claims:

At Column 13, line 11, "isoproponal" should be -- isopropanol --.

Signed and Sealed this
Twenty-eighth Day of June, 2016

Michelle K. Lee
*Director of the United States Patent and Trademark Office*